US012661478B2

(12) United States Patent
Benkoski et al.

(10) Patent No.: US 12,661,478 B2
(45) Date of Patent: Jun. 23, 2026

(54) REGENERABLE CARBON DIOXIDE SCRUBBER

(71) Applicant: The Johns Hopkins University, Baltimore, MD (US)

(72) Inventors: Jason J. Benkoski, Catonsville, MD (US); Paul J. Biermann, Columbia, MD (US); William L. Luedeman, New Market, MD (US); Jeffrey M. Paulson, Columbia, MD (US); Steven M. Storck, Timonium, MD (US); Melanie L. Morris, Odenton, MD (US); Evan D. Jacque, Columbia, MD (US); Michael H. Jin, Ellicott City, MD (US); Reginald Beach, Arlington, VA (US)

(73) Assignee: The Johns Hopkins University, Baltimore, MD (US)

( * ) Notice: Subject to any disclaimer, the term of this patent is extended or adjusted under 35 U.S.C. 154(b) by 1104 days.

(21) Appl. No.: 17/188,411

(22) Filed: Mar. 1, 2021

(65) Prior Publication Data

US 2022/0273906 A1 Sep. 1, 2022

(51) Int. Cl.
*A61M 16/22* (2006.01)
*B01D 53/04* (2006.01)

(52) U.S. Cl.
CPC ......... *A61M 16/22* (2013.01); *B01D 53/0438* (2013.01); *B01D 2257/504* (2013.01); *B01D 2259/40088* (2013.01); *B01D 2259/4541* (2013.01)

(58) Field of Classification Search
CPC ............ A61M 16/1005; A61M 16/125; A61M 16/208; A61M 16/22; A61M 2016/103; A61M 2202/0208; A61M 2209/088; B01D 53/0407; B01D 53/0415; B01D 53/0438; B01D 53/0462; B01D 2257/504; B01D 2258/06; B01D 2259/40088; B01D 2259/4541; Y02C 20/40
See application file for complete search history.

(56) References Cited

U.S. PATENT DOCUMENTS

| | | | | |
|---|---|---|---|---|
| 3,944,400 A | * | 3/1976 | Bird ........................ | C01B 23/00 96/111 |
| 4,172,454 A | * | 10/1979 | Warncke .............. | A62B 17/005 2/457 |
| 6,041,777 A | * | 3/2000 | Faithfull ........... | A61M 16/0054 128/200.24 |
| 7,520,280 B2 | * | 4/2009 | Gordon ................... | B63C 11/24 128/201.27 |

(Continued)

*Primary Examiner* — Timothy A Stanis
*Assistant Examiner* — Matthew D Ziegler
(74) *Attorney, Agent, or Firm* — Todd R. Farnsworth

(57) ABSTRACT

A regenerable carbon dioxide scrubber includes at least a first housing compartment including an inlet, an outlet, and an interior region. A sorbent material is located within the interior region of the first housing compartment, in which the sorbent material (a) attracts and/or retains carbon dioxide from an air supply passing through the sorbent material at an operating temperature below about 100° C. and (b) releases carbon dioxide at a regenerating temperature above about 150° C. A rebreather including the regenerable carbon dioxide scrubber may be used to scrub carbon dioxide from a user's exhaled air.

20 Claims, 13 Drawing Sheets

(56)                    References Cited

U.S. PATENT DOCUMENTS

| | | | |
|---|---|---|---|
| 7,698,905 B1 * | 4/2010 | Carpenter | A61F 7/02 |
| | | | 62/259.3 |
| 8,424,515 B1 * | 4/2013 | MacCallum | F24F 5/0007 |
| | | | 128/201.13 |
| 8,678,001 B2 | 3/2014 | Cowgill | |
| 9,901,899 B2 * | 2/2018 | Kwon | B01D 53/62 |
| 10,195,468 B2 * | 2/2019 | Allan | A62B 9/00 |
| 2006/0026743 A1 * | 2/2006 | Farnworth | A41D 31/145 |
| | | | 2/455 |
| 2009/0095300 A1 * | 4/2009 | McMorrow | A61M 16/0045 |
| | | | 128/205.12 |
| 2010/0012124 A1 * | 1/2010 | Deas | A62B 9/006 |
| | | | 128/204.22 |
| 2017/0313027 A1 * | 11/2017 | Silvia | B32B 27/40 |
| 2020/0246572 A1 * | 8/2020 | Scheiner | A61M 16/0611 |

* cited by examiner

REGENERABLE CARBON DIOXIDE SCRUBBER

STATEMENT OF GOVERNMENTAL INTEREST

This invention was made with Government support under contract number N00014-19-1-2215 awarded by the Office of Naval Research. The Government has certain rights in the invention.

TECHNICAL FIELD

Embodiments of the presently-disclosed invention relate generally to regenerable carbon dioxide scrubbers including a sorbent material that can be thermally regenerated in-place after use, rebreathers including such regenerable carbon dioxide scrubbers, methods of scrubbing carbon dioxide from a user's exhaled air, and methods of performing a task in an oxygen gas-reduced environment.

BACKGROUND

Breathing uses chemical and mechanical processes to bring oxygen to every cell of the human body and to get rid of carbon dioxide. Our body needs oxygen to obtain energy to fuel all our living processes, while carbon dioxide is a waste product of that process. In this regard, people naturally produce carbon dioxide upon breathing. The amount of carbon dioxide produced depends on the person's work load (e.g., level or intensity of bodily work). At rest, for example, a human body may only produce about 0.3 to 0.5 L/min or carbon dioxide, for moderate work it may be around 1.5 L/min, and during hard or substantial physical work, the body may produce about 4 L/min.

The common way to remove carbon dioxide from a diver's rebreather, for example, is by chemically reacting the carbon dioxide with various soda lime formulations (e.g., Sofnolime®). Soda lime formulations, for example, react chemically with carbon dioxide to form a carbonate. Essentially, each mole of calcium hydroxide (74 g) reacts with one mole of carbon dioxide (44 g) to form one mole of calcium carbonate and water. Once the soda lime formulations have been spent (e.g., used up via reaction with carbon dioxide), the soda lime formulations within the rebreather need to be replaced with new material. That is, the canister housing the soda lime formulation is opened, the soda lime formulation material is disposed of, and new (unused) soda lime formulation material is packed into the canister of the rebreather.

SUMMARY OF THE DISCLOSURE

Certain embodiments according to the invention provide a regenerable carbon dioxide scrubber including at least one housing compartment, in which the at least one housing compartment includes a first housing compartment. The first housing compartment may include an inlet, an outlet, and an interior region. The regenerable carbon dioxide scrubber may also include a sorbent material located within the interior region of the first housing compartment. The sorbent material (i) attracts and/or retains carbon dioxide from an air supply passing through the sorbent material at an operating temperature below about 100° C., and (ii) releases carbon dioxide at a regenerating temperature above about 150° C.

In one aspect, the invention provides a rebreather including a mouthpiece operatively connected to an inlet of a regenerable carbon dioxide scrubber. The regenerable carbon dioxide scrubber includes at least one housing compartment, in which the at least one housing compartment includes a first housing compartment. The first housing compartment may include the inlet that is operatively connected to the mouthpiece, an outlet, and an interior region. The regenerable carbon dioxide scrubber may also include a sorbent material located within the interior region of the first housing compartment. The sorbent material (i) attracts and/or retains carbon dioxide from an air supply passing through the sorbent material at an operating temperature below about 100° C., and (ii) releases carbon dioxide at a regenerating temperature above about 150° C. The rebreather may also include an inhalation counter-lung (ICL) including an ICL-inlet and an ICL-outlet, in which the ICL-inlet is operatively connected to the outlet of the first housing compartment of the regenerable carbon dioxide scrubber and the ICL-outlet is operatively connected to the mouthpiece.

In another aspect, the invention provides a method of scrubbing carbon dioxide from a user's exhaled air. The method may include the following: (i) providing a regenerable carbon dioxide scrubber as described and disclosed herein; (ii) receiving the user's exhaled air and directing the user's exhaled air into that at least one housing compartment, wherein the user's exhaled air has a first carbon dioxide concentration; and (iii) allowing the user's exhaled air to pass through the sorbent material and exit the at least one housing compartment via the outlet of the at least one housing compartment to provide a stream of carbon dioxide-scrubbed air, wherein the stream of carbon dioxide-scrubbed air has a second carbon dioxide concentration that is less than the first carbon dioxide concentration.

In yet another aspect, the invention provides a method of performing a task in an oxygen gas-reduced environment. The method may include the following: (i) providing a regenerable carbon dioxide scrubber as described and disclosed herein; (ii) receiving the user's exhaled air and directing the user's exhaled air into that at least one housing compartment, wherein the user's exhaled air has a first carbon dioxide concentration; and (iii) allowing the user's exhaled air to pass through the sorbent material and exit the at least one housing compartment via the outlet of the at least one housing compartment to provide a stream of carbon dioxide-scrubbed air, wherein the stream of carbon dioxide-scrubbed air has a second carbon dioxide concentration that is less than the first carbon dioxide concentration. In accordance with certain embodiments of the invention, the task may comprise underwater diving, spacewalks, extinguishing a fire, or cleaning a chemical spill.

BRIEF DESCRIPTION OF THE DRAWING(S)

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements Like numbers refer to like elements throughout, and wherein.

Figure 3:
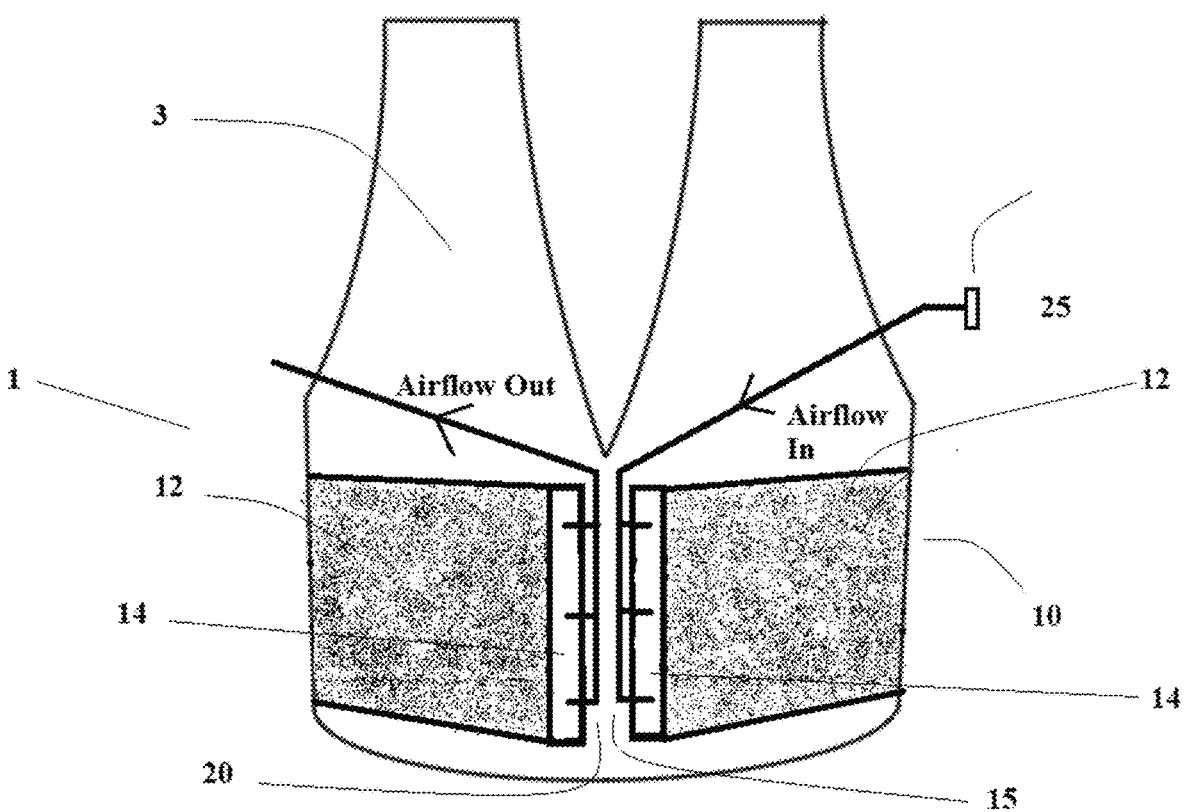
Figure 4:
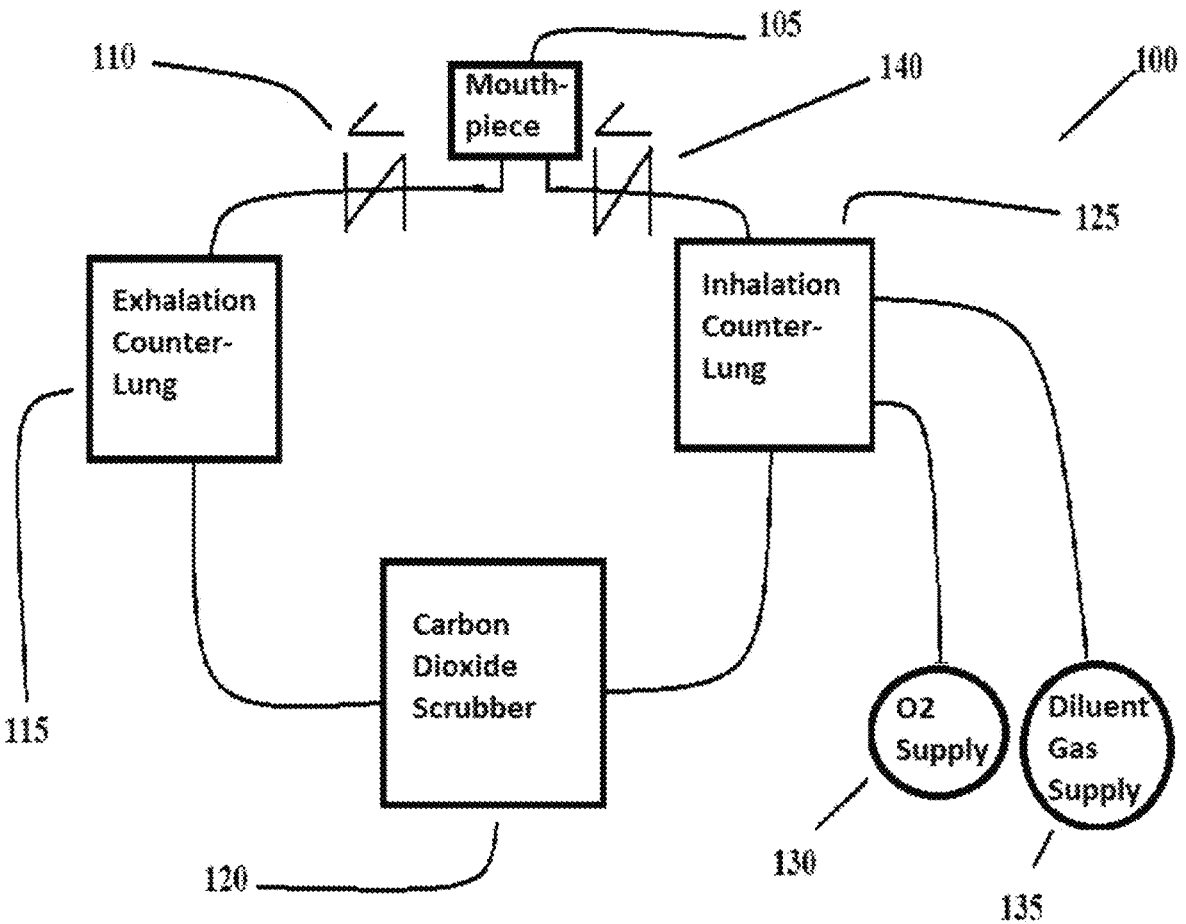
Figure 5:
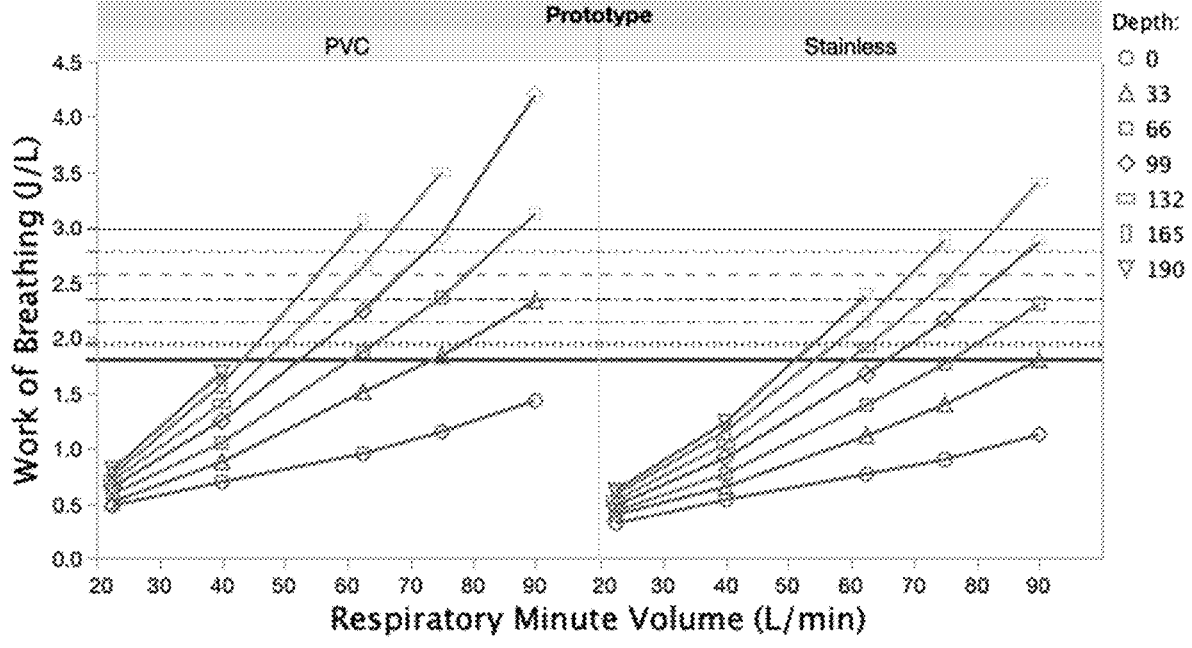
Figure 6:
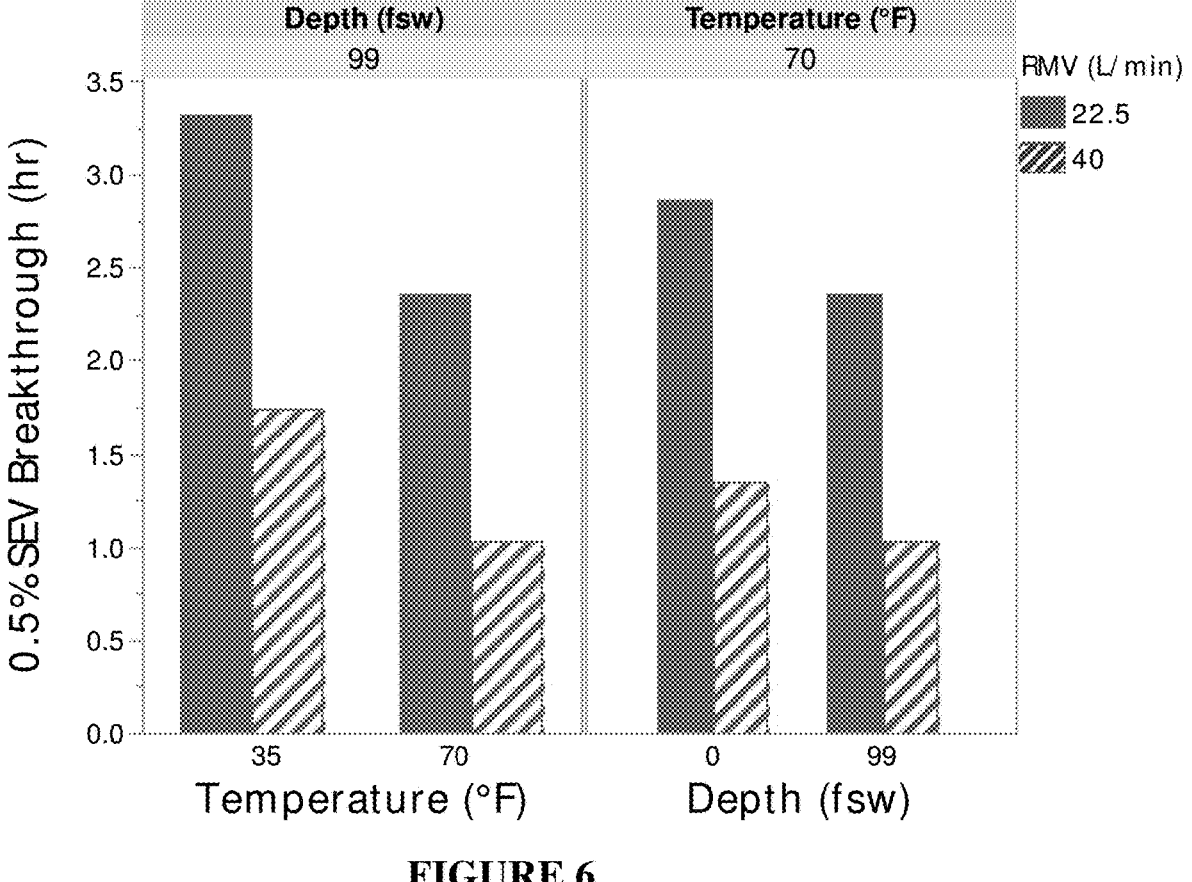
Figure 7:
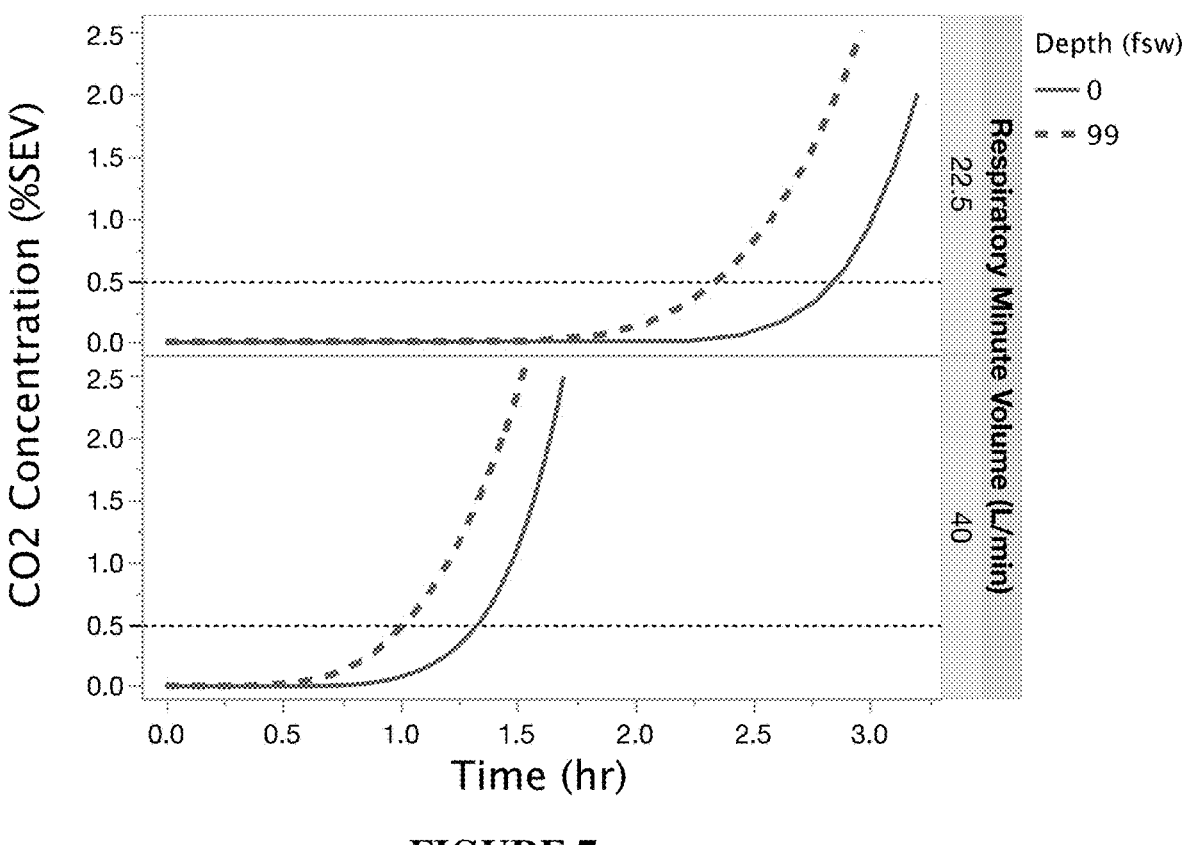
Figure 8:
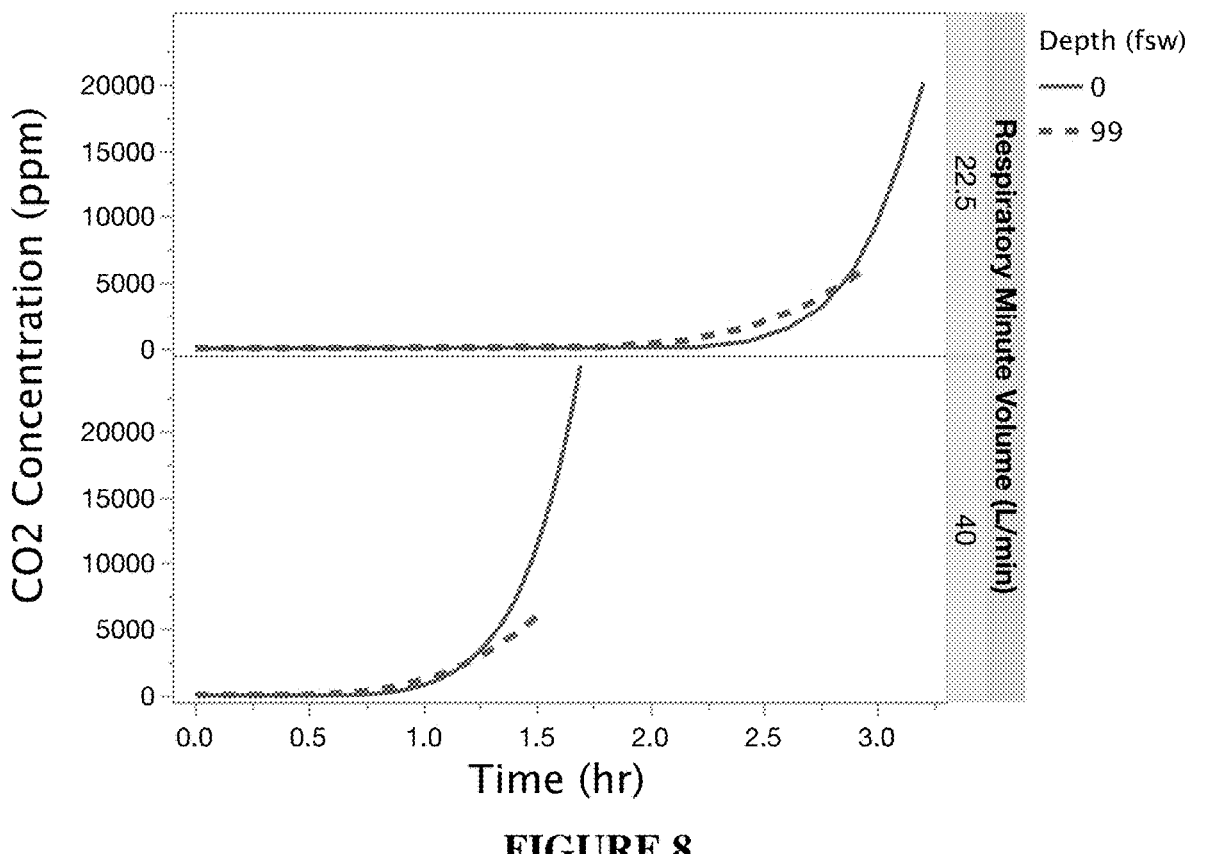
Figure 9A:
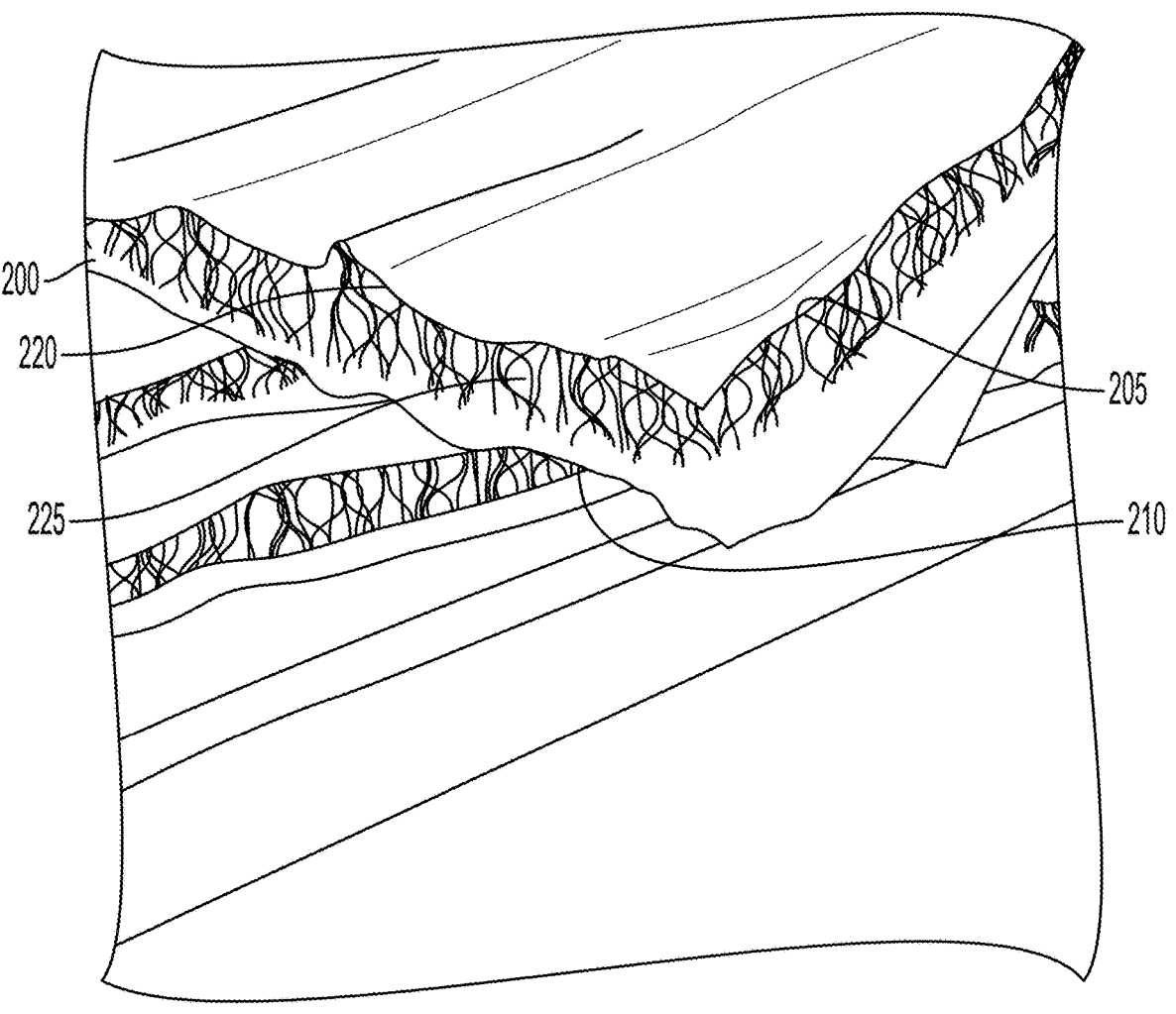
Figure 9B:
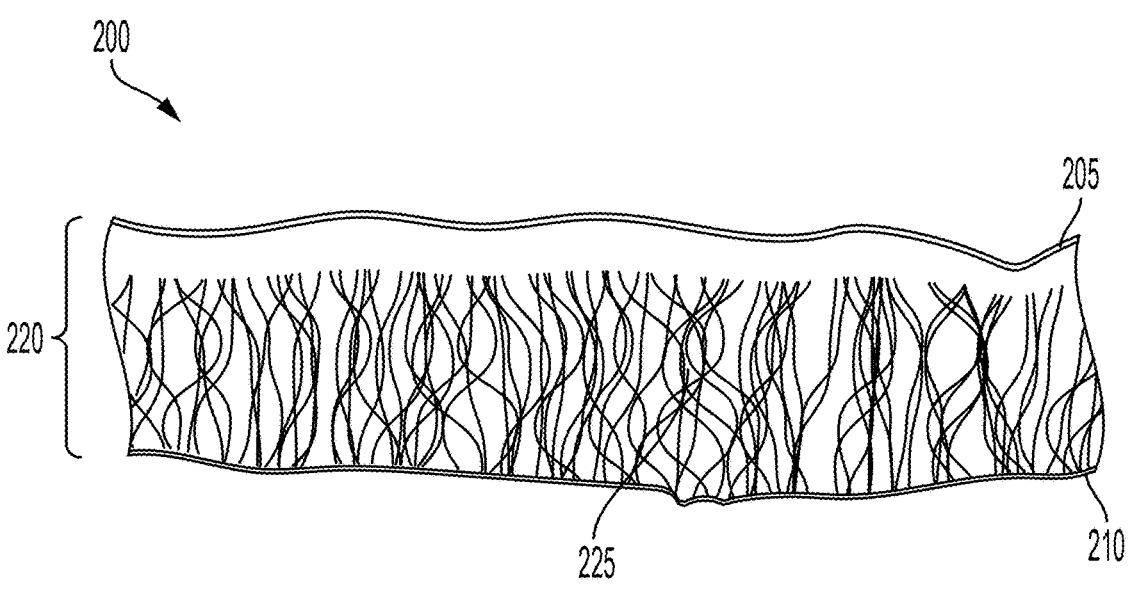
Figure 10:
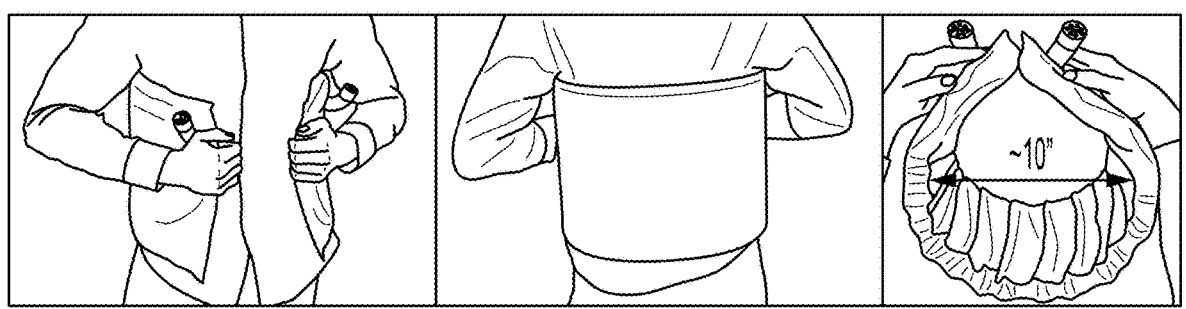
Figure 11A:
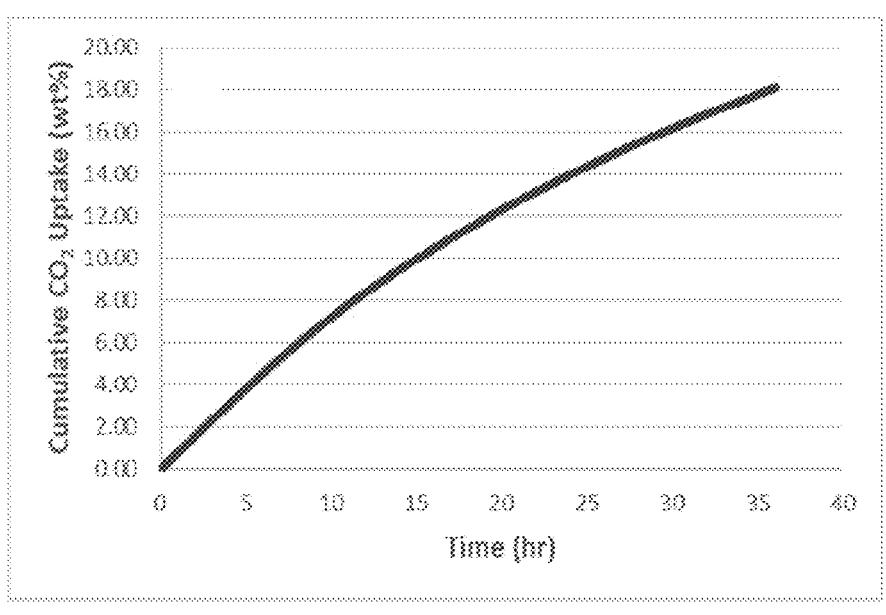
Figure 11B:
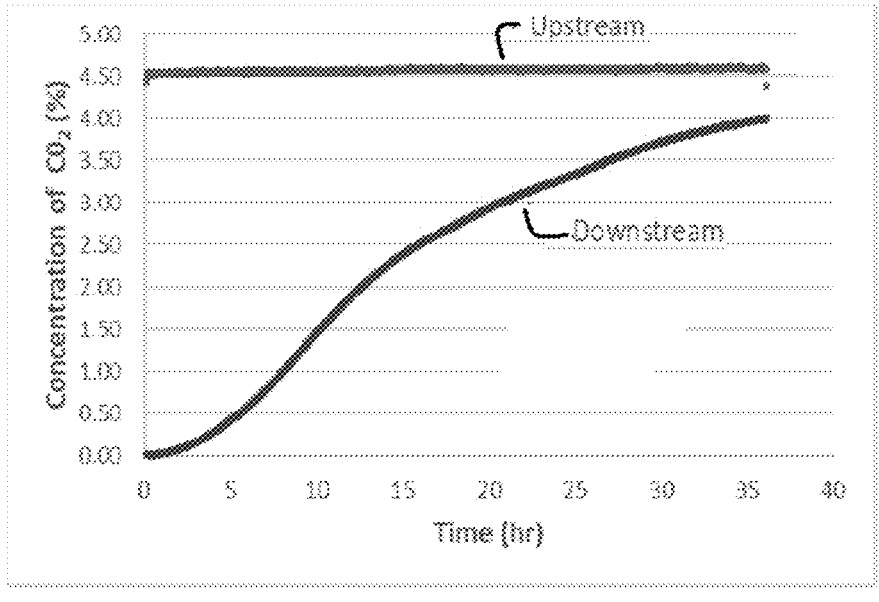
Figure 12:
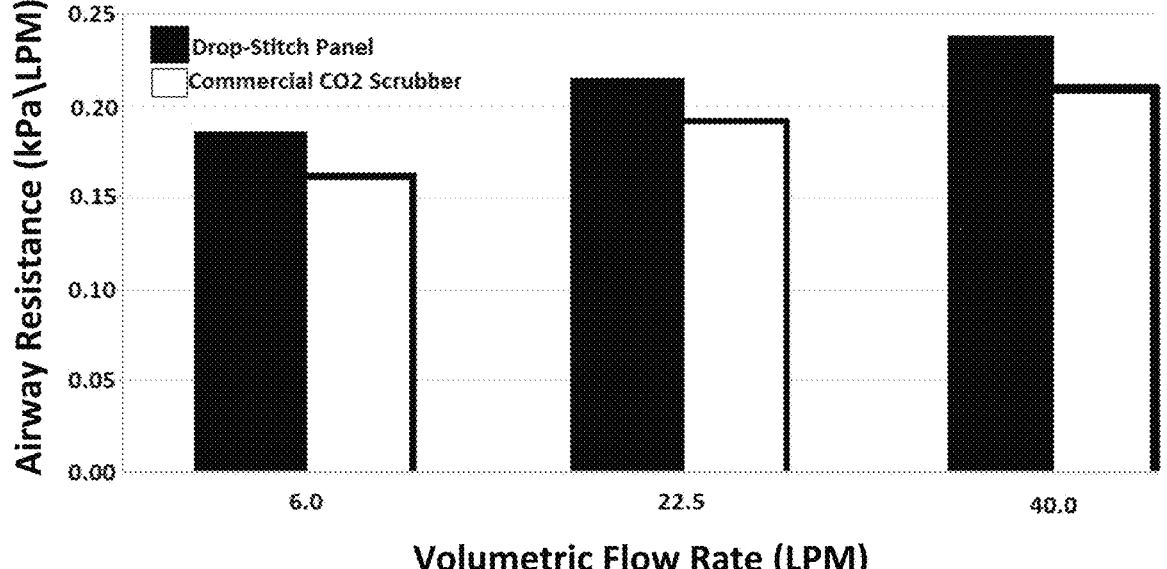
Figure 13:
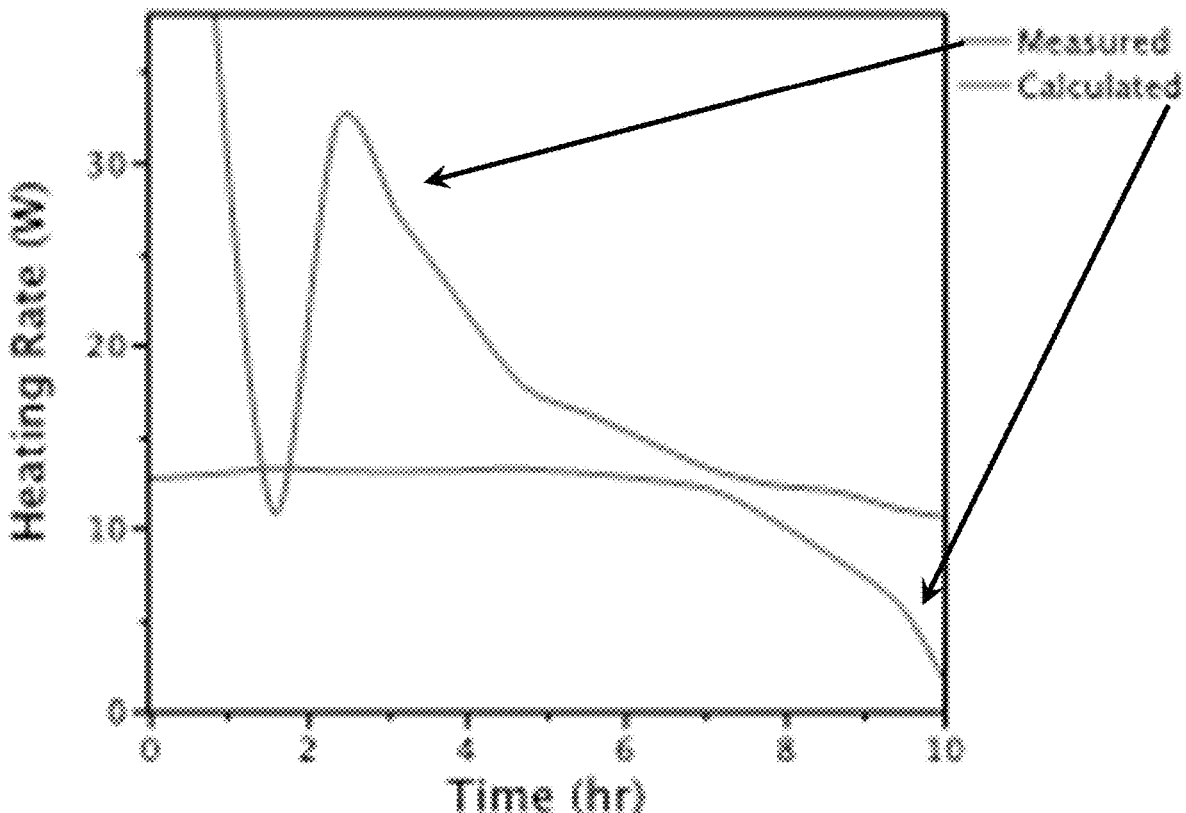

FIG. 3 another regenerable carbon dioxide scrubber according to certain embodiments of the invention;

FIG. 4 illustrates a schematic of rebreather in accordance with certain embodiments of the invention;

FIG. 5 shows plots of work of breathing as a function of respiratory volume at various pressures for two example embodiments;

FIG. 6 shows the 0.5% SEV breakthrough for an example embodiment for various respiratory volumes at two different temperatures and two pressures;

FIG. 7 shows the plot of carbon dioxide concentration as a function of time for two different respiratory volumes and two different pressures;

FIG. 8 shows the plot of carbon dioxide concentration in ppm as a function of time for two different respiratory volumes and two different pressures;

FIGS. 9A and 9B show an example drop-stitch fabric in accordance with certain embodiments of the invention;

FIG. 10 shows an example regenerable carbon dioxide scrubber according to certain embodiments of the invention;

FIG. 11A shows a plot of cumulative carbon dioxide uptake by an example embodiment as a function of time;

FIG. 11B shows a plot of the carbon dioxide concentration both upstream and downstream from an example regenerable carbon dioxide scrubber;

FIG. 12 illustrates the airway resistance through an example embodiment for various respiratory volumes; and FIG. 13 shows a plot of heat released over time during carbon dioxide scrubbing from an example embodiment.

DETAILED DESCRIPTION

Embodiments of the invention now will be described more fully hereinafter with reference to the accompanying drawings, in which some, but not all embodiments of the invention are shown. Indeed, the present invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

Embodiments of the present invention relate generally regenerable carbon dioxide scrubbers that can be used for underwater divers, astronauts, firefighters, first responders, or other oxygen gas poor areas. Unlike current carbon dioxide scrubbers where the single-use scrubbing materials need to be replaced after use, the present invention provides regenerable carbon dioxide scrubbers that may be used to capture carbon dioxide, thermally regenerated (e.g., in-place such that the sorbent material does not need to be removed from the carbon dioxide scrubber), and re-used for the capture of carbon dioxide again. In accordance with certain embodiments of the invention, the regenerable carbon dioxide scrubbers include a sorbent material that attracts and/or retains gaseous carbon dioxide from an air stream under certain operating temperatures and can release the attracted and/or retained carbon dioxide upon being thermally regenerated. In accordance with certain embodiments of the invention, the regenerable carbon dioxide scrubbers may also provide heat to a user wearing a regenerable carbon dioxide scrubber. For example, the regenerable carbon dioxide scrubbers may be configured or provided in the form of a wearable article. In this regard, the regenerable carbon dioxide scrubber can be positioned adjacent or proximate to a user, such as an underwater diver, and the thermal energy liberated from the scrubbing action of the sorbent material (e.g., retention of the carbon dioxide within or on the surface of the sorbent material) is transferred to the user. By way of example only, the regenerable carbon dioxide scrubber may be provided in the form of a vest or a tubular form. In accordance with certain embodiments of the invention, the regenerable carbon dioxide scrubber can be worn inside an outer article of clothing, such as a diver's dry suit, a space suit, a flame retardant coat, or a chemically resistant coat. For underwater divers, for example, the regenerable carbon dioxide scrubber can be worn inside the diver's dry suit like a vest and supply passive heating to the diver in cold-water conditions while simultaneously scrubbing carbon dioxide from the diver's exhaled air. In accordance with certain embodiments of the invention, the regenerable carbon dioxide scrubbers maybe incorporated as a component of a full rebreather.

In accordance with certain embodiments to the invention, a regenerable carbon dioxide scrubber includes one or more housing compartments, in which at least one or all of the housing compartments include one or more sorbent materials contained therein. In this regard, the one or more housing compartments may comprise a first housing compartment. The first housing compartment may include an inlet, an outlet, and an interior region. The regenerable carbon dioxide scrubber, as noted above, may also include a sorbent material located within the interior region of the first housing compartment. In accordance with certain embodiments of the invention, the sorbent material (i) attracts and/or retains carbon dioxide from an air supply passing through the sorbent material at an operating temperature, in which the operating temperature may comprise the temperature of the sorbent material and/or the temperature of the air passing through the sorbent material, below about 100° C., such as at least about any of the following: 0, 5, 10, 15, 20, 25, 30, 35, 40, 45, 50, 55, 60, 70, 80, 85, and 90° C. and/or at most about 100, 98, 96, 94, 92, and 90° C., and (ii) releases carbon dioxide at a regenerating temperature above about 150° C., such as above at least about any of the following: 150, 175, 200, 225, 250, 270, 300, 325, and 350° C. and/or at most about any of the following: 500, 475, 450, 425, 400, 375 and 350° C. (e.g., 270-375° C., 300-350° C., 350-400° C., etc.). In this regard, the sorbent material may attract and/or retain (e.g., absorb and/or adsorb) gaseous carbon dioxide from an air stream at an operating temperature and release the previously attracted and/or retained gaseous carbon dioxide from the sorbent material at a regenerating temperature, which is higher than the operating temperature. In accordance with certain embodiments of the invention, the regenerable nature of the sorbent material, at least in part, enables the regenerable carbon dioxide scrubber to be used multiple times without any need to replace or replenish the sorbent material. For example, the regenerable carbon dioxide scrubber may be used to scrub carbon dioxide from a user's exhaled air during a first task (e.g.,. underwater diving), regenerated, re-used for a subsequent or second task (e.g., underwater diving), regenerated for a second time, re-used for a third task, regenerated for a third time, and so on.

In accordance with certain embodiments of the invention, the regenerable carbon dioxide scrubber includes at least one housing compartment, which may comprise a gas-tight structure. In this regard, exhaled air from a user that passes through the regenerable carbon dioxide scrubber is not allowed to leak out the walls of the one or more housing compartments and is forced to travel through the sorbent material that may be packed inside the housing compartment(s). For example, the at least one housing compartment may comprise a hermetically sealed compartment, (e.g., no air can leave or enter it) with the exception of desired inlets and outlets to allow (i) exhaled air to enter into that regenerable carbon dioxide scrubber at one or more desired locations and (ii) to exit the regenerable carbon dioxide scrubber at one or more desired locations as scrubbed air (e.g., reduced carbon dioxide concentration relative to the user exhaled air that entered the regenerable carbon dioxide scrubber). In this regards, the term "hermetically sealed compartment" may refer to a compartment that has one or more walls that do not let air into or out of the compartment, but may include inlet and outlet ports and/or valves configured to collectively channel an air stream into, thru, and out of the regenerable carbon dioxide scrubber. The inlet and outlet ports and/or valves may comprise one-way valves directly or be directly or indirectly connected to one-way valves to ensure a single direction of air flow through the regenerable carbon dioxide scrubber.

In accordance with certain embodiments of the invention, the at least one housing compartment may comprise a polymeric shell, a fabric, or a rubber housing. For example, the at least one housing compartment may comprise, a drop-stitch material, which may be hermetically sealed. In accordance with certain embodiments of the invention, the drop-stitch material resists expansion or deformation due to changes in internal pressure, at least in part, due to a plurality of individual drop-stitches mechanically connecting a first exterior wall of the drop-stitch material and a second exterior wall of the drop-stitch material. In this regard, the drop-stitch material may formed from a variety of fibers and/or yarns that are provided in the form of a drop-stitch fabric that includes a first exterior wall, a second exterior wall, and a plurality of drop stitches that extend in a generally perpendicular direction from the first exterior wall to the second exterior wall. The plurality of drop stitches, therefore, connect the first and second exterior walls together and, at least in part, define a maximum gap or distance between the first and second exterior walls. Beneficially, the fixed or controlled maximum gap or distance between the first and second exterior walls provides one mechanism to resist expansion or deformation due to changes in internal pressure (e.g., from internal air that may wish to form pockets while submerged underwater). In accordance with certain embodiments of the invention, for example, the combination of the first exterior wall, the second exterior wall, and the plurality of drop stitches define a rectangular gap having a substantially uniform maximum thickness between the first exterior wall and the second external wall. The first and second exterior walls of the drop-stitch material, for instance, may define exterior walls for the at least one housing compartment. In accordance with certain embodiments of the invention, the first exterior wall of the drop-stitch material may define a user-facing wall for the at least one housing compartment and the second external wall of the drop-stitch material may define an environment-facing wall of the at least one housing compartment.

Additionally or alternatively, the at least one housing compartment may further comprise an external or internal support structure or structures that facilitate or provide a maximum gap or distance the user-facing wall and the environment-facing wall of the at least one housing compartment. For example, the at least one housing compartment have include one or more braces that may be located internally or externally to the at least one housing structure. For instance, the one or more braces may comprise a plurality of supporting components (e.g., rectangular wires) that wrap around the at least one housing component, which may be hermetically sealed component, in an accordion-like structure that resembles, for example, a whale-bone corset. Such externally located supporting components may ensure a maximum uniform gap or distance between the user-facing wall and the environment-facing wall. Additionally or alternatively, the at least one housing compartment may be formed over and/or around such a system of support structures. Additionally or alternatively, the braces may comprises a plurality of internal columns that may be discrete or interconnected as part of a grid structure.

In accordance with certain embodiments of the invention, the at least one housing compartment may comprise a substantially rectangular cross-section for an air supply passing through the at least one housing compartment. For instance, the interior region(s) of the at least one housing compartment may comprise a substantially rectangular cross-section. In accordance with certain embodiments of the invention, the substantially rectangular cross-section may be facilitated or provided by a variety of mechanisms (e.g., drop-stitches, brace(s), etc.). The substantially rectangular cross-section for an air supply passing through the at least one housing compartment provides a means for preventing undesirable formation of air-pockets within the at least one housing. Formation of air-pockets within the at least one housing compartment, for instance, may constitute dead-zones in which the carbon dioxide within the air is not removed in an, at least, efficient manner. Additionally, the formation of air-pockets within the at least one housing compartment may negatively impact the wearability and/or ease of use in, for example, underwater diving operations.

As noted above, the at least one housing compartment may comprise exterior walls that include a user-facing wall and an environment-facing wall, in which a thickness between the user-facing wall and the environment-facing wall is substantially constant (e.g., substantially rectangular cross-section with a uniform maximum distance between the first and second exterior walls) in accordance with certain embodiments of the invention. The substantially constant thickness between the user-facing wall and the environment-facing wall may be ensured by defining a maximum gap or distance therebetween as discussed above. In this regard, the substantially constant thickness or gap between the user-facing wall and the environment-facing wall may comprise from about 0.5 to about 6 inches, such as at least about any of the following: 0.5, 0.75, 1, 1.25, 1.5, 1.75, 2, 2.5, 3, and 3.5 inches, and/or at most about any of the following: 6, 5.5, 5, 4.5, 4, and 3.5 inches. As used herein, the phrase "substantially constant" may comprise a deviation from an average value of thickness or from an predetermined thickness of no more than about 10% or no more than about 20% over an operable area of more than about 80%, 90%, 95%, or 100%, in which the operable area comprises a region in which sorbent material is provided between the user-facing wall and the environment-facing wall. For instance, the user-facing wall and the environment-facing wall may be adjoined directed together at one or more seams and these regions would not be considered as defining part of the operating area.

As noted above, the at least one housing compartment may comprise a fabric, such as a drop-stitch fabric, that may be formed from a variety of fibers and/or yarns. In accordance with certain embodiments of the invention, the at least one housing compartment may comprise a plurality of fibers, plurality of yarns, or both, in which they may optionally comprise a high-temperature resistant material. In this regard, the plurality of fibers and/or yarns may themselves be formed directly from the high-temperature resistant material or the plurality of fibers and/or yarns may be externally coated with the high-temperature resistant material (e.g., a coating of the high-temperature material may be disposed on the surface of the fibers and/or yarns). In accordance with certain embodiments of the invention, the optional high-temperature resistant material (e.g., forming the fibers or yarns themselves or as a coating on the fibers or yarns) is not necessarily limited. In accordance with certain embodiments of the invention, for example, the high-temperature resistant material does not degrade at temperatures associated with regeneration of the sorbent material. In accordance with certain embodiments of the invention, for instance, the high-temperature resistant material has a degradation temperature that is larger than the regenerating temperature, such as greater than the regenerating temperature by about 20° C. to about 300° C. For example, the high-temperature resistant material may withstand temperatures of above about 150° C. to about 600° C., such as at least about any of the following: 150, 175, 200, 225, 250, 270, 300, 325, and 350° C., and/or at most about any of the following: 600, 550, 500, 450, 400, and 350° C. Non-limiting examples of high-temperature resistant materials from which a plurality of fibers and/or yarns may be directly formed include may include a polyamide, a polyimide, or any combination thereof. In accordance with certain embodiments of the invention, the sorbent material may be regenerated separately from the at least one housing compartment. For instance, the sorbent material may be removed from the at least one housing compartment and regenerated separately (e.g., within an oven). In such embodiments, for instance, the plurality of fibers, plurality of yarns, or both would not be subjected to the elevated temperature associated with regeneration of the sorbent material. Accordingly, in such embodiments, the plurality of fibers, plurality of yarns, or both would not need to be formed from or include any coating of a high-temperature resistant material.

Drop-stitch fabrics, in accordance with certain embodiments of the invention, may comprise three-dimensional woven fabrics. In this regard, the drop-stitch fabric may include two skins (e.g., external walls) that may be simultaneously woven and spaced apart by a distance governed by the length of the drop yarns. The drop yarns, which are a second family of warp yarns woven within the skins, are periodically "dropped" from one skin to the other skin and repeated in an alternating manner. In accordance with certain embodiments of the invention, the skins (e.g., external walls) may be coated with an elastomeric or polymeric material to form airtight skins (e.g., external walls). In accordance with certain embodiments of the invention, the elastomeric or polymeric material may comprise a high-temperature resistant material as described and discussed herein. The skins, in accordance with certain embodiments of the invention, may comprise or consist of a base fabric that comprises a plain-woven fabric using, for example, two orthogonal yarn directions referred to as warp and a weft directions and a second warp yarn family included for the drop yarns and/or drop fibers. In accordance with certain embodiments of the invention, the drop-stich fabric may comprise a height or distance between the two skins (e.g., outer walls) from about 0.25 inches to about 6 inches, such as at least about any of the following: 0.25, 0.5, 1, 1.5, 2, 2.5, and 3 inches, and/or at most about any of the following: 6, 5.5., 5, 4.5, 4, 3.5, and 3 inches. Additionally or alternatively, the dropstitch fabric may comprise a drop-stitch density (e.g., number of drop yarns extending between and connecting the two skins per square inch of the drop stitch fabric) of from about 5 to 50 yarns/in², such as at least about any of the following: 5, 8, 10, 12, 15, 18, 20, 22, 25, 28, and 30 yarns/in², and/or at most about any of the following: 50, 48, 45, 42, 40, 38, 35, 32, and 30 yarns/in².

The at least one housing compartment, in accordance with certain embodiments of the invention, may comprise a plurality of external surfaces that include a polymer coating positioned thereon. In accordance with certain embodiments of the invention, the at least one housing compartment may comprise a plurality of internal surfaces that may include the polymer coating positioned thereon. For example the plurality of external surfaces and/or the plurality of internal surfaces may include a polymer coated thereon. The polymer coating, for example, may facilitate and/or form a gas-tight seal or barrier. In accordance with certain embodiments of the invention, the polymer coating on the external surfaces of the at least one housing compartment has a degradation temperature that is larger than the regenerating temperature, such as greater than the regenerating temperature by about 20° C. to about 300° C. For example, the polymer coating on the external surfaces of the at least one housing compartment may withstand temperatures of above about 150° C. to about 600° C., such as at least about any of the following: 150, 175, 200, 225, 250, 260, 270, 300, 325, and 350° C., and/or at most about any of the following: 600, 550, 500, 450, 400, and 350° C. In this regard, the polymer coating is compatible with the elevated temperatures associated with regeneration of the sorbent material. Although the polymer coating is not particularly limited, the polymer coating may comprise a silicone in accordance with certain embodiments of the invention.

Figure 1:
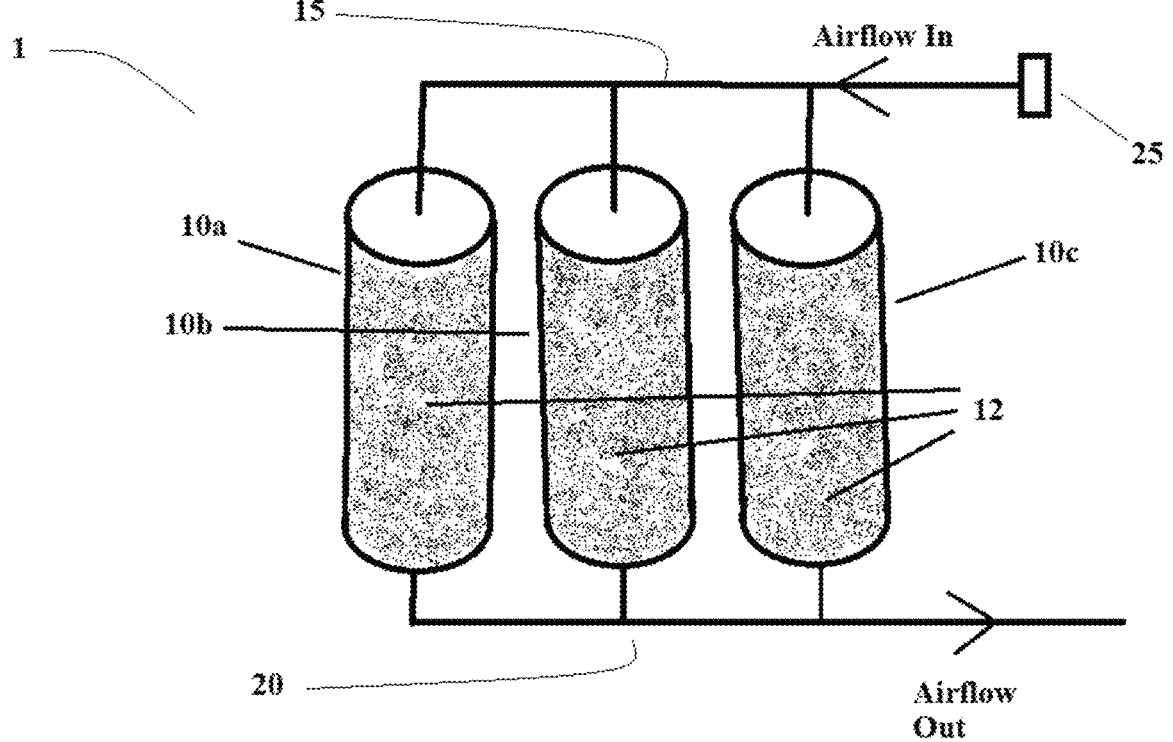
FIG. 1 illustrates a regenerable carbon dioxide scrubber according to certain embodiments of the invention.

FIG. 1 illustrates a regenerable carbon dioxide scrubber 1 in accordance with certain embodiments of the invention. As shown in FIG. 1, the regenerable carbon dioxide scrubber 1 includes a plurality of separate and distinctly individual housing compartments 10a, 10b, 10c, in which each housing compartment includes a sorbent material 12 contained therein. The regenerable carbon dioxide scrubber 1 includes an inlet manifold 15 operatively coupled to each housing compartment 10a, 10b, 10c and a source of exhaled air 25 (e.g., mouthpiece receiving exhaled air from a user). The regenerable carbon dioxide scrubber 1 also includes an outlet manifold 20 that allows air to exit each of the housing compartments 10a, 10b, 10c. As shown in FIG. 1, the housing compartments 10a, 10b, 10c are configured in a parallel orientation or configuration such that an air stream from the source of exhaled air 25 is spit into separate streams (e.g., evenly split among the number of housing compartments), passed thru the respective housing compartment, and recombined as a single stream of air flow via the outlet manifold 20.

Figure 2:
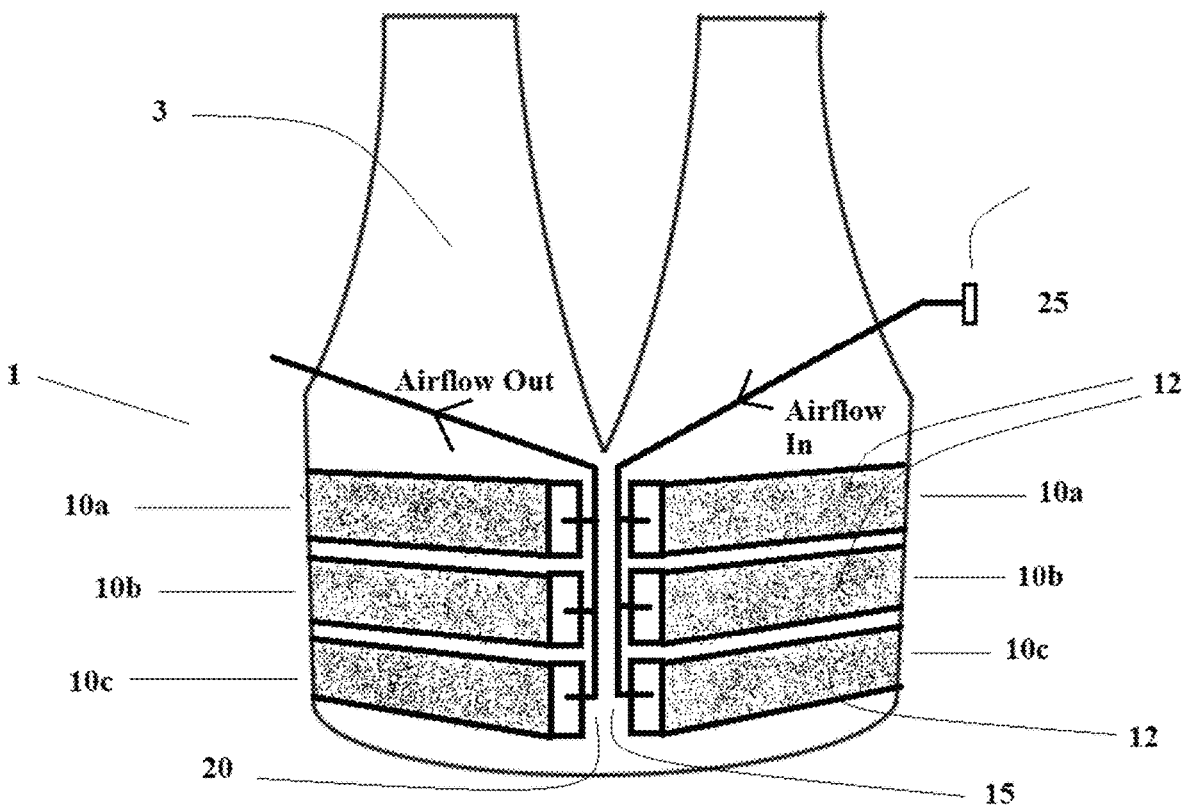
FIG. 2 illustrates another regenerable carbon dioxide scrubber according to certain embodiments of the invention.

Although FIG. 1 illustrates a regenerable carbon dioxide scrubber 1 having cylindrical housing compartments 10a, 10b, 10c that are not incorporated into a wearable article of clothing, FIG. 2 illustrates a regenerable carbon dioxide scrubber 1 that is incorporated within or part of a wearable article 3 (e.g., a vest). The regenerable carbon dioxide scrubber 1 illustrated by FIG. 2 includes a includes a plurality of separate and distinctly individual housing compartments 10a, 10b, 10c, in which each housing compartment includes a sorbent material 12 contained therein. As shown in FIG. 2, each housing compartment 10a, 10b, 10c have a rectangular cross-section with inlets located at a first side of the vest 3, extend around the backside of the vest, and end on the second side of the vest where the airstreams exit the respective housing compartments 10a, 10b, 10c. The regenerable carbon dioxide scrubber 1 includes an inlet manifold 15 operatively coupled to each housing compartment 10a, 10b, 10c and a source of exhaled air 25 (e.g., mouthpiece receiving exhaled air from a user). The regenerable carbon dioxide scrubber 1 also includes an outlet manifold 20 that allows air to exit each of the housing compartments 10a,10b, 10c. As shown in FIG. 2, the housing compartments 10a, 10b, 10c are configured in a parallel orientation or configuration such that an air stream from the source of exhaled air 25 is spit into separate streams (e.g., evenly split among the number of housing compartments), passed thru the respective housing compartment, and recombined as a single stream of air flow via the outlet manifold 20.

As generally illustrated by FIGS. 1 and 2, for instance, the at least one housing compartment may comprise a plurality of separate and distinct individual housing compartments, in which each of the individual housing compartments may comprise a respective inlet, a respective outlet, and a respective interior region. Each of the respective interior regions may be filled at least partially (or completely) with the sorbent material. In embodiments including a plurality of separate and distinct individual housing compartments, each separate and distinct individual housing compartments may be operatively coupled in a parallel configuration through an inlet manifold and optionally an outlet manifold as illustrated in FIGS. 1 and 2.

FIG. 3 illustrates a regenerable carbon dioxide scrubber 1 according to certain embodiments of the invention including a single housing compartment 10 that contains a sorbent material 12 therein. The regenerable carbon dioxide scrubber 1 shown in FIG. 3 is provided within or as a part of a wearable article 3 (e.g., a vest). The single housing compartment 10 has rectangular cross-section 14 and starts on a first side of the vest, extends around the backside of the vest, and ends on the second side of the vest. The regenerable carbon dioxide scrubber 1 includes an inlet manifold 15 operatively coupled to the housing compartment and a source of exhaled air 25 (e.g., mouthpiece receiving exhaled air from a user). As shown in FIG. 3, the inlet manifold may distribute the total airflow from the source of exhaled air 25 evenly or by a predefined distribution of airflow across the cross-section of the housing compartment. For instance, controlling the distribution of the airflow across the cross-section of the housing compartment may prevent localized channeling of airflow in which one section of sorbent material may be exposed to a greater volume of airflow than another resulting in ineffective use of all of the sorbent material in the housing compartment. In accordance with certain embodiments of the invention, the inlet manifold may be configured to provide a substantially uniform airflow across substantially the entire cross-section of the housing compartment.

Although FIGS. 2 and 3 illustrate housing compartment(s) having an inlet, airflow pathway, and outlet oriented in a side-to-side configuration, certain embodiments of the invention may include one or more housing compartments having an inlet, airflow pathway, and outlet oriented in a top-to-bottom configuration or a bottom-to-top configuration (e.g., inlet being located proximate or at a shoulder portion of a jacket and an outlet at or proximate a waist portion of a jacket or vice versa). In accordance with certain embodiments of the invention, the article of clothing including a regenerable carbon dioxide scrubber may comprise a vest, a portion of a vest, an overcoat, a portion of an overcoat, a backpack, a portion of a backpack, shorts, pants, or headgear.

In accordance with certain embodiments of the invention, the inlet to the housing compartment(s) may be operatively connected to a mouthpiece for use by an individual and the outlet from the housing compartment(s) may be operatively connected to a mixing-chamber, wherein the mixing-chamber is also operatively connected to an oxygen gas supply.

In accordance with certain embodiments of the invention, the sorbent material absorbs and/or adsorbs carbon dioxide (e.g., gaseous carbon dioxide) at the operating temperature and releases carbon dioxide (e.g., gaseous carbon dioxide) at the regenerating temperature. The sorbent material, in accordance with certain embodiments of the invention, may comprise a plurality of individual porous substrates (e.g., particles). In accordance with certain embodiments of the invention, the plurality of individual porous substrates comprise a zeolite, a metal-organic framework (MOF), a silica, an amine-functional resin, or any combination thereof. For example, the sorbent material comprises a Type A zeolite, such as a Type 3A zeolite, a Type 4A zeolite, a Type 5A zeolite, or any combination thereof. Additionally or alternatively, the sorbent material may comprise a Type X zeolite, such as a Type 13X zeolite, a Type 10X zeolite, or any combination thereof. Additionally or alternatively, the sorbent material may comprise one or more MOFs, wherein the one of more MOFs include a plurality of metal ions or clusters of metal ions coordinated to one or more organic ligands. In accordance with certain embodiments of the invention, the one or more organic ligands may comprise a monovalent ligand, a divalent ligand, a trivalent ligand, a tetravalent ligand, or any combination thereof.

In accordance with certain embodiments of the invention, the sorbent material comprises a carbon dioxide retaining capacity from at least about 0.01 grams of carbon dioxide per gram of the sorbent material, such as from at least about any of the following: 0.01, 0.05, 0.08, 0.1, 0.15, 0.2, 0.3, 0.4, and 0.5 grams of carbon dioxide per gram of sorbent material, and/or at most about any of the following: 2, 1.5, 1, 0.75, and 0.5 grams of carbon dioxide per gram of sorbent material. Additionally or alternatively, the sorbent material comprises a carbon dioxide retaining capacity from at least about 0.002 grams of carbon dioxide per $cm^3$ of the sorbent material, such as from at least about any of the following: 0.002, 0.005, 0.008, 0.01, 0.02, 0.03, 0.04, and 0.05 grams of carbon dioxide per $cm^3$ of sorbent material, and/or at most about any of the following: 1, 0.75, 0.5, 0.25, 0.1, and 0.5 grams of carbon dioxide per $cm^3$ of sorbent material.

In another aspect, the invention provides a rebreather including a mouthpiece operatively connected to an inlet of a regenerable carbon dioxide scrubber, such as any of those disclosed and described herein. The regenerable carbon dioxide scrubber includes at least one housing compartment, in which the at least one housing compartment includes a first housing compartment. The first housing compartment may include the inlet that is operatively connected to the mouthpiece, an outlet, and an interior region. The regenerable carbon dioxide scrubber may also include a sorbent material located within the interior region of the first housing compartment. The sorbent material (i) attracts and/or retains carbon dioxide from an air supply passing through the sorbent material at an operating temperature, in which the operating temperature may comprise the temperature of the sorbent material and/or the temperature of the air passing through the sorbent material, below about 100° C., such as at least about any of the following: 0, 5, 10, 15, 20, 25, 30, 35, 40, 45, 50, 55, 60, 70, 80, 85, and 90° C. and/or at most about 100, 98, 96, 94, 92, and 90° C., and (ii) releases carbon dioxide at a regenerating temperature above about 150° C., such as above at least about any of the following: 150, 175, 200, 225, 250, 270, 300, 325, and 350° C. and/or at most about any of the following: 500, 475, 450, 425, 400, 375 and 350° C. (e.g., 270-375° C., 300-350° C., 350-400° C., etc.).

The rebreather may also include an inhalation counter-lung (ICL) including an ICL-inlet and an ICL-outlet, in which the ICL-inlet is operatively connected to the outlet of the first housing compartment of the regenerable carbon dioxide scrubber and the ICL-outlet is operatively connected to the mouthpiece.

In accordance with certain embodiments of the invention, the rebreather may further comprise an exhalation counter-lung (ECL) including an ECL-inlet and an ECL-outlet, in which the ECL-inlet is operatively connected to the mouth-piece and the ECL-outlet is operatively connected to the inlet of the carbon dioxide scrubber. The rebreather may also comprise an oxygen gas addition supply directly or indirectly operatively connected to the ICL. Additionally or alternatively, the rebreather may comprise a diluent gas addition supply directly or indirectly operatively connected to the ICL. In accordance with certain embodiments of the invention, the rebreather may comprise a first one-way valve operatively connected to the mouthpiece and a second one-way valve operatively connected to the mouthpiece, in which the first one-way valve is oriented to allow an airflow to only travel towards the carbon dioxide scrubber inlet and the second one-way valve is oriented to allow the airflow to travel from the carbon dioxide scrubber outlet towards the mouthpiece.

FIG. 4 illustrates a schematic of rebreather 100 in accordance with certain embodiments of the invention. The rebreather includes a mouthpiece 105 that is operatively connected to an inlet of an ECL 115. A first one-way valve 110 may be located between the mouthpiece 105 and the inlet of the ECL 115. The rebreather also includes a regenerable carbon dioxide scrubber 120, in which the outlet of the ECL 115 is operatively connected to an inlet of the regenerable carbon dioxide scrubber. As shown in FIG. 4, the rebreather also includes and ICL 125, in which an inlet to the ICL is operatively coupled to the regenerable carbon dioxide scrubber 120 and an outlet of the ICL is operatively connected to the mouthpiece 105. An oxygen supply 130 and a diluent gas supply 135 may optionally be operatively connected to the ICL 125. The rebreather may also include a second one-way valve 140 positioned between the mouth-piece 105 and the ICL 125. As shown in FIG. 4, the airflow through the rebreather travels in a counter-clockwise manner.

In another aspect, the invention provides a method of scrubbing carbon dioxide from a user's exhaled air. The method may include the following: (i) providing a regenerable carbon dioxide scrubber, such as described and disclosed herein; (ii) receiving the user's exhaled air and directing the user's exhaled air into at least one housing compartment, wherein the user's exhaled air has a first carbon dioxide concentration; and (iii) allowing the user's exhaled air to pass through the sorbent material and exit the at least one housing compartment via the outlet of the at least one housing compartment to provide a stream of carbon dioxide-scrubbed air, wherein the stream of carbon dioxide-scrubbed air has a second carbon dioxide concentration that is less than the first carbon dioxide concentration.

In accordance with certain embodiments of the invention, the at least one housing compartment comprises an article of clothing or a portion of an article of clothing as disclosed and described herein, wherein the at least one housing compartment may be located proximate or adjacent to the user. During use of the regenerable carbon dioxide scrubber, the sorbent material may attract and/or retain gaseous carbon dioxide from the user's exhaled air to strip or scrub carbon dioxide from the user's exhaled air. In this regard, the active retention of carbon dioxide within or on the surface of the sorbent material comprises an exothermic process giving off heat which may be used to warm the user during use. FIG. 13 shows a plot of heat released during carbon dioxide scrubbing from an example embodiment. The data in FIG. 13 was collected in an example embodiment under 4.35% $CO_2$ and 70% relative humidity in air at a constant breathing rate of 6 L/min. In accordance with certain embodiments of the invention, the method may further comprise providing heat liberated during the retention of the carbon dioxide within or on the surface of the sorbent material to the user. In this regard, the external surface of the at least one housing compartment proximate to the environment (e.g., the side farthest away from the user) may directly or indirectly include a material having a higher thermal resistivity than the surface of the at least one housing compartment proximate or facing the user. Additionally or alternatively, the external surface of the at least one housing compartment proximate to the environment (e.g., the side farthest away from the user) may be covered by a thermally insulating layer or shell. Such configurations, for example, facilitate the channeling or movement of heat liberated by the carbon dioxide retention process towards the user (e.g., an underwater diver).

In accordance with certain embodiments of the invention, the method may comprise monitoring the carbon dioxide concentration in the stream of carbon dioxide-scrubbed air and providing an indication in response to detection of a predetermined threshold of carbon dioxide in the stream of carbon dioxide-scrubbed air. The method may also comprise regenerating the sorbent material in response to detection of a predetermined threshold of carbon dioxide in the stream of carbon dioxide-scrubbed air. In accordance with certain embodiments of the invention, the step of regenerating the sorbent material may comprise heating the sorbent material to an elevated temperature that is sufficient to initiate the release of carbon dioxide retained on the sorbent material. For example, the elevated temperature may comprise at least about 150° C. to about 600° C. , such as at least about any of the following: 150, 175, 200, 225, 250, 270, 300, and 350° C., and/or at most about any of the following: 600, 550, 500, 450, 400, 375, and 350° C. In accordance with certain embodiments of the invention, the method may comprise a step of forcing a gaseous mobile phase (e.g., air or an inert gas) through the sorbent material during at least a portion of the regenerating step to facilitate removal of carbon dioxide from the at least one housing compartment. In this regard, the gaseous mobile phase may function in a manner to flush out any unattached carbon dioxide from the at least one housing compartment.

In yet another aspect, the invention provides a method of performing a task in an oxygen gas-reduced environment. The method may include the following: (i) providing a regenerable carbon dioxide scrubber as described and disclosed herein; (ii) receiving the user's exhaled air and directing the user's exhaled air into at least one housing compartment, wherein the user's exhaled air has a first carbon dioxide concentration; and (iii) allowing the user's exhaled air to pass through the sorbent material and exit the at least one housing compartment via the outlet of the at least one housing compartment to provide a stream of carbon dioxide-scrubbed air, wherein the stream of carbon dioxide-scrubbed air has a second carbon dioxide concentration that is less than the first carbon dioxide concentration. In accordance with certain embodiments of the invention, the task may comprise underwater diving, spacewalks, extinguishing a fire, or cleaning a chemical spill.

EXAMPLES

The present disclosure is further illustrated by the following examples, which in no way should be construed as being limiting. That is, the specific features described in the following examples are merely illustrative and not limiting.

Example Set 1

A low temperature regenerable carbon dioxide scrubber prototype, in which the sorbent must be removed for regeneration was prepared as well as a high temperature regenerable carbon dioxide scrubber prototype, in which the sorbent can be regenerated in place, were constructed. In this regard, the housing compartments of the low temperature regenerable carbon dioxide scrubber prototype was formed from PVC tubing (i.e., five 1.5 inch diameter PVC tubes were used as housing compartments), while the high temperature regenerable carbon dioxide scrubber prototype was formed from stainless steel tubing (i.e., six 1.5 inch diameter stainless steel tubes were used as housing compartments). Zeolite 5A was the sorbent material used in both prototypes. That is, each of the tubes in each prototype was filled with zeolite 5A as the regenerable sorbent material.

Work of Breathing

A breathing simulator supplied a sinusoidal flow function to a rebreather including one of the regenerable carbon dioxide scrubber prototypes. The breathing simulator controlled the respiratory minute volume to 22.5, 40, 62.5, 75, or 90 L/min. The pressure was adjusted from 1 to 7 atm, corresponding to 0 to 190 feet of seawater. The temperature was maintained at 70° F. for all tests. FIG. 5 illustrates the work of breathing plotted versus breathing rate for different depths, up to 190 feet of sea water (fsw). The low temperature PVC prototype had a work of breathing value that was about 20% higher than that of the high temperature stainless steel prototype.

As seen in FIG. 5, the two prototypes met standard work of breathing requirements for most operationally relevant conditions. The low temperature PVC prototype passed the requirements up to 75 L/min and 66 feet of sea water (fsw). The high temperature stainless steel prototype, with 6 hoses instead of 5, passed requirements up to 75 L/min and 99 fsw. Both met requirements up to 40 L/min and 190 fsw. The high temperature stainless steel prototype having the 6-hose configuration was about 20% better than the low temperature PVC prototype having the 5-hose configuration. In this regard, it is believed that the addition of additional tubes of sorbent material would further reduce the work of breathing.

Carbon Dioxide Capacity

Zeolite 5A can capture about 10% of its mass in carbon dioxide during normal usage. As such, 8.3 pounds of this sorbent material can fit into a cylindrical volume having dimensions of 15 inches tall by 36 inches long and 1.5 inches deep. The carbon dioxide capacity should have theoretically been fixed to about 0.8 pounds of carbon dioxide. The prototypes were actually able to capture a full pound of carbon dioxide, meaning that the efficiency of the sorbent material was closer to 12%. This efficiency is much closer to the 13% theoretical efficiency of Zeolite 5A. The 0.5% carbon dioxide surface equivalent volume (SEV) breakthrough time, however, was still relatively short. FIG. 6 shows that the longest breakthrough time was 3.3 hours at a breathing rate of 22.5 L/min, 99 fsw, and 35° F. The shortest time was 1 hour at 40 L/min, 99 fsw, and 70° F. One interesting point illustrated by FIG. 6 includes that the Zeolite 5A performs better with decreasing temperature. At reduced temperatures, thermal fluctuations have a lower probability of ejecting carbon dioxide molecules from the surface. As such, the application of such regenerable carbon dioxide scrubbers in applications having colder environments (e.g., underwater diving, spacewalks, etc.) may be particularly desirable.

Effects of Depth on Carbon Dioxide Capacity

One original concern for the use of Zeolite 5A as the sorbent material was that greater depths may decrease the diffusivity of carbon dioxide to the point where carbon dioxide scrubbing would become diffusion limited. Since carbon dioxide must diffuse 2 mm to reach the center of each Zeolite 5A bead, a slow diffusion rate could mean that the sorbent was only partially utilized before the gas traverses completely through the column of sorbent material.

FIGS. 7 and 8, however, shows that pressure had almost no effect in going from 1 to 4 atm (0 to 99 fsw). One could look at the reduction in 0.5% SEV breakthrough time and mistakenly think that the carbon dioxide capacity decreased at the greater depth. In fact, the difference is only due to the correction that is applied to the SEV concentration due to the difference in pressure. If one looks at the absolute concentration in ppm, then the carbon dioxide absorption is nearly the same at both depths. In particular, FIG. 7 plots the carbon dioxide concentration in % SEV as a function of time at 0 and 99 fsw. FIG. 8 plots the carbon dioxide concentration in ppm as a function of time at 0 and 99 fsw. Interestingly, the plotted lines overlap at both depths when the absolute concentration of carbon dioxide is considered.

Effects of Breathing Rate on Carbon Dioxide Capacity

The second concern for the Zeolite 5A was whether it could remove carbon dioxide fast enough to keep up with faster breathing rates. FIGS. 7 and 8 show that breathing rate was not a problem. The Zeolite 5A was able to scrub carbon dioxide with only a small drop off in performance in going from 22.5 to 40 L/min. This result was especially impressive given the known difficulties of removing carbon dioxide in the presence of moisture. Additionally, the use of Zeolite 13X desiccant in combination with Zeolite 5A was also considered. The Zeolite 13X desiccant was able to remove water fast enough so that 98° F. air at 100% relative humidity could flow through the tubes at a rate of 40 L/min without poisoning the Zeolite 5A.

When the carbon dioxide concentration is plotted versus the cumulative uptake of carbon dioxide in grams, one can see that the 0.5% breakthrough occurs at slightly longer times. This difference indicates that carbon dioxide scrubbing is still diffusion limited at these ventilation rates, but not catastrophically so.

Example Set 2

Fabrication of Drop-Stitch Material from a High-temperature Fiber

A drop-stitch fabric was formed from Technora® T240 fibers produced by Teijin Aramid, which is desired to withstand a sorbent regeneration process at a temperature as high as 300° C. Theses fibers were found to provide (1) excellent mechanical and thermal properties, (2) comparability with high-temperature polymer coating utilized for making the housing compartments gas-tight, (3) commercial availability (357 lb of 400 denier Technora® yarn necessary for the development in the loom for producing the drop-stitch fabric), and (4) cost ($40/lb), which is competitive to other high-performance fibers rated for lower temperatures. Technora®, aromatic copolyamide manufactured by a spinning process, is a high-performance para-aramid fiber with exceptional strength, resistance to heat and chemicals, long-term dimensional stability and abrasion resistance. It has very high tenacity (2200 mN/tex), a measure of specific strength of a fiber or yarn, compared to other aramid fibers and also offers excellent flexibility and fatigue resistance necessary for weave-ability. It has a decomposition temperature of ~500° C., and it does not experience shrinkage when exposed to hot air, which is important for the high-temperature sorbent regeneration process.

High Temperature Coating Materials

High-temperature coating materials may be used to make the drop-stitch fabrics gas-tight. For the current example, silicone was used as the coating material because it has been proven effective at high temperatures on different materials. Silicone compounds offer performance in a wide temperature range, such as up to approximately 300° C. depending on formulation, and are suited for applications requiring low gas permeability, thermal aging stability, high flexibility, and abrasion resistance.

Weaving Method

A weaving process for Technora® fiber was employed and 12 yards of drop-stitch fabric was woven. FIGS. 9A and 9B show the drop-stitch fabric 200, which includes a first exterior wall 205, a second exterior wall 210, and a plurality of drop-stitches 225, 215 interconnecting the first and second exterior walls. In this regard, the plurality of drop-stitches 225, 215 define or set a uniform maximum gap or distance 220 between the first and second exterior walls 205 and 210. The drop-stitch shown in FIG. 9A and 9B has a height 220 of 1.3 inches and the drop-stitch density is 26 yarns/in².

Fabrication of a Drop-Stitch Sample Panel

While the weaving process for Technora® fiber was being performed for the high-temperature housing compartments, a low temperature drop-stitch prototype was fabricated using polyurethane-coated nylon materials. While the prototype cannot handle the targeted regeneration temperature at 300° C., it allowed evaluation of carbon dioxide capacity and airway resistance in parallel to completion of the high-temperature Technora® fiber prototype. The panel, shown in FIG. 10, had dimensions of 39 inches by 12.5 inches by 1.3 inches, which was the size specified for the final high-temperature prototype to be fabricated. As shown in FIG. 10, the panel could be wrapped around the torso of an adult male comfortably, and the drop-stitch prevents any ballooning upon introduction of the sorbents. The internal volume of the panel was 0.37 ft³, which is ~1.6× larger than the tubular prototype described in Example Set 1 discussed above. This configuration allows for more volume available for sorbents, which should increase the total carbon dioxide capacity and breakthrough time. If necessary, the volume could be further increased by making the panel thicker than 1.3 inches, facilitating integration of even more sorbents and also lowering the work of breathing. The pictures of the panel shown in FIG. 10 illustrate that two 90-degree thermoplastic polyurethane valves were welded on the panel in order to insert sorbents to the panel and to flow the air through it. The drop-stitch density was 30 yarns/in². The panel was filled with 15.8 lb (7.2 kg) of the Zeolite sorbents.

Testing Sorbents in Drop-Stitch Based Housing Compartment

The test version of the drop-stitch sample panel was tested for its carbon dioxide capacity and airway resistance. First objectives to answer included: i) how uniformly the sorbents in the panel would be consumed, and ii) whether or not there would be any spike in carbon dioxide concentration in the downstream air flow before breakthrough due to potential preferential consumption of the sorbents in the panel (i.e., a vest). The panel was filled with 12.1 lb of Zeolite sorbents (5A from Delta Absorbents) and tested under dry air to verify its baseline performance. The total amount of carbon dioxide absorbed at the end of the run was 9.6 lb, 18% of initial amount of the sorbents (FIG. 11A). Although the total capacity was unusually high, 5% higher than the 'statically' measured capacity previously, the high capacity indicates that the air was flowing through the entire panel in a fairly uniform fashion. Additionally, FIG. 11B shows no carbon dioxide spike in the downstream all the way through the end of the carbon dioxide capacity, indicating no preferential air pathways exist in the panel.

The airway resistance of the drop-stitch panel was also calculated and compared to a commercial carbon dioxide scrubber. FIG. 12 shows that the drop-stitch panel has airway resistance only 14-20% higher than that of the commercial scrubber. A 2 inch diameter tubular prototype fabricated previously provided airway resistance lower than the commercial scrubber, so leveraging insights form that previous prototype it is likely that increasing the thickness of the drop stitch panel from 1.3 inches to 1.5 inches could lead to a decrease in air resistance.

These and other modifications and variations to embodiments of the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

That which is claimed:

1. A regenerable carbon dioxide scrubber, comprising:

at least one housing compartment comprising an inlet, an outlet, and an interior region fluidly coupling the inlet and the outlet, wherein the at least one housing compartment is defined by a drop-stitch fabric comprising:

a first exterior wall, a second exterior wall, wherein the first exterior wall is configured to be user-facing and the second exterior wall is configured to be environment-facing, and a plurality of drop-stitches mechanically connecting the first exterior wall and the second exterior wall, the plurality of drop-stitches defining a maximum gap between the first and second exterior walls to form an interior region having a substantially uniform maximum thickness, and to resist expansion or deformation of the housing compartment due to changes in internal pressure, an inlet manifold fully coupled to the inlet of the housing compartment, wherein the inlet manifold is configured to distribute airflow into the housing compartment such that the airflow is substantially uniform across substantially an entire cross-section of the housing compartment, and a sorbent material located within the interior region of the housing compartment, wherein the sorbent material (a) attracts and/or retains carbon dioxide from an air supply passing through the sorbent material at an operating temperature below about 100° C., and (b) releases carbon dioxide at a regenerating temperature above about 150° C.

2. The scrubber of claim 1, wherein the at least one housing compartment comprises a gas-tight structure.

3. The scrubber of claim 1, wherein the at least one housing compartment comprises a substantially rectangular cross-section for an air supply passing through the at least one housing compartment.

4. The scrubber of claim 1, wherein the drop-stich stitch fabric comprises a plurality of fibers, yarns, or both; and wherein the plurality of fibers, yams yarns, or both are formed from a high-temperature resistant materials that withstand temperatures above at least about 150° C.

5. The scrubber of claim 1, wherein the plurality of exterior walls include a polymer coating positioned thereon.

6. The scrubber of claim 5, wherein the polymer coating defines a gas-tight barrier and withstands temperatures of at least about 150° C.

7. The scrubber of claim 6, wherein the polymer comprises a silicone.

8. The scrubber of claim 1, wherein the at least one housing compartment comprises a plurality of separate and distinct individual housing compartments, and each of the individual housing compartments comprises a respective inlet, a respective outlet, and a respective interior region; wherein each respective interior region is filled at least partially with the sorbent material.

9. The scrubber of claim 8, wherein the plurality of separate and distinct individual housing compartments are operatively coupled in a parallel configuration through an inlet manifold.

10. The scrubber of claim 1, wherein the sorbent material comprises a plurality of individual porous substrates, and wherein the sorbent material absorbs and/or adsorbs carbon dioxide at the operating temperature and releases carbon dioxide at the regenerating temperature.

11. The scrubber of claim 10, wherein the plurality of individual porous substrates comprise a zeolite, a metal-organic framework (MOF), a silica, an amine-functional resin, or any combination thereof.

12. A method of performing a task in an oxygen gas-reduced environment using a regenerable carbon dioxide scrubber according to claim 1, the method comprising:

receiving exhaled air by a user and directing the exhaled air into that at least one housing compartment, wherein the exhaled air has a first carbon dioxide concentration; and allowing the exhaled air to pass through the sorbent material and exit the at least one housing compartment via the outlet of the at least one housing compartment to provide a stream of carbon dioxide-scrubbed air; wherein the stream of carbon dioxide-scrubbed air has a second carbon dioxide concentration that is less than the first carbon dioxide concentration, wherein the task comprises underwater diving, space-walks, extinguishing a fire, or cleaning a chemical spill.

13. The scrubber of claim 1, wherein the at least one housing compartment is capable of wrapping around a torso of a user.

14. The scrubber of claim 1, wherein the at least one housing compartment is incorporated within or part of an article of clothing or a component of an article of clothing and the article of clothing is capable of being worn inside of an outer article of clothing.

15. A rebreather, comprising:

a mouthpiece operatively connected to an inlet of a regenerable carbon dioxide scrubber; and an inhalation counter-lung (ICL) including an ICL-inlet and an ICL-outlet, the ICL-inlet is operatively connected to an outlet of the carbon dioxide scrubber and the ICL-outlet is operatively connected to the mouth-piece, wherein the regenerable carbon dioxide scrubber comprises:

at least one housing compartment comprising an inlet, an outlet, and an interior region fluidly coupling the inlet and the outlet, wherein the at least one housing compartment is defined by a drop-stitch fabric comprising:

a first exterior wall, a second exterior wall, wherein the first exterior wall is configured to be user-facing and the second exterior wall is configured to be environment-facing, and a plurality of drop-stitches mechanically connecting the first exterior wall and the second exterior wall, the plurality of drop-stitches defining a maximum gap between the first and second exterior walls to form an interior region having a substantially uniform maximum thickness, and to resist expansion or deformation of the housing compartment due to changes in internal pressure, an inlet manifold fully coupled to the inlet of the housing compartment, wherein the inlet manifold is configured to distribute airflow into the housing compartment such that the airflow is substantially uniform across substantially an entire cross-section of the housing compartment, a sorbent material located within the interior region of the first housing compartment; wherein the sorbent material attracts and/or retains carbon dioxide from an air supply passing through the sorbent material at an operating temperature below about 100° C., and releases carbon dioxide at a regenerating temperature above about 150° C.

16. The rebreather of claim 15, further comprising an exhalation counter-lung (ECL) including an ECL-inlet and an ECL-outlet, the ECL-inlet is operatively connected to the mouthpiece and the ECL-outlet is operatively connected to the inlet of the carbon dioxide scrubber.

17. A method of scrubbing carbon dioxide from a user's exhaled air using a regenerable carbon dioxide scrubber, the regenerable carbon dioxide scrubber comprising:

at least one housing compartment comprising an inlet, an outlet, and an interior region fluidly coupling the inlet and the outlet, the at least one housing compartment is defined by a drop-stitch fabric comprising:

a first exterior wall, a second exterior wall, wherein the first exterior wall is configured to be facing a user and the second exterior wall is configured to be environment-facing, and a plurality of drop-stitches mechanically connecting the first exterior wall and the second exterior wall, the plurality of drop-stitches defining a maximum gap between the first and second exterior walls to form an interior region having a substantially uniform maximum thickness, and to resist expansion or deformation of the housing compartment due to changes in internal pressure, an inlet manifold fully coupled to the inlet of the housing compartment, wherein the inlet manifold is configured to distribute airflow into the housing compartment such that the airflow is substantially uniform across substantially an entire cross-section of the housing compartment, wherein the at least one housing compartment is incorporated within or part of an article of clothing proximate or adjacent to the user, wherein the article of clothing is configured to be worn at least on one of a side of a torso of a user, a front of the torso of the user, a leg of the user, or a head of the user; and a sorbent material located within the interior region of the housing compartment; wherein the sorbent material attracts and/or retains carbon dioxide from an air supply passing through the sorbent material at an operating temperature below about 100° C., and releases carbon dioxide at a regenerating temperature above about 150° C.;

the method comprising:

receiving the user's exhaled air and directing the user's exhaled air into the at least one housing compartment, wherein the user's exhaled air has a first carbon dioxide concentration; and allowing the user's exhaled air to pass through the sorbent material and exit the at least one housing compartment via the outlet of the at least one housing compartment to provide a stream of carbon dioxide-scrubbed air, wherein the stream of carbon dioxide-scrubbed air has a second carbon dioxide concentration that is less than the first carbon dioxide concentration.

18. The method of claim 17, further comprising providing heat to the user associated with retention of carbon dioxide by the sorbent material.

19. The method of claim 17, further comprising monitoring the second carbon dioxide concentration in the stream of carbon dioxide-scrubbed air and providing an indication in response to detection of a predetermined threshold of carbon dioxide in the stream of carbon dioxide-scrubbed air.

20. The method of claim 17, wherein the article of clothing comprises a first article of clothing, and wherein the first article of clothing is configured to be worn inside of a second article of clothing.

\* \* \* \* \*